(12) United States Patent
Willenburg et al.

(10) Patent No.: US 11,925,529 B2
(45) Date of Patent: Mar. 12, 2024

(54) DEVICES AND METHODS FOR ARTIFICIAL INSEMINATION

(71) Applicant: Inguran, LLC, Navasota, TX (US)

(72) Inventors: Kilby Willenburg, DeForest, WI (US); Christian Rudolf Simmet, Landshut (DE); Gregg Bevier, Navasota, TX (US); Dominik Armbruster, Tiefenbach (DE)

(73) Assignee: Inguran, LLC, Navasota, TX (US)

( * ) Notice: Subject to any disclaimer, the term of this patent is extended or adjusted under 35 U.S.C. 154(b) by 878 days.

(21) Appl. No.: 16/555,855

(22) Filed: Aug. 29, 2019

(65) Prior Publication Data

US 2020/0069407 A1    Mar. 5, 2020

Related U.S. Application Data

(60) Provisional application No. 62/725,829, filed on Aug. 31, 2018.

(51) Int. Cl.
*A61D 19/02* (2006.01)
*A61L 29/06* (2006.01)
*A61M 25/00* (2006.01)

(52) U.S. Cl.
CPC .......... *A61D 19/028* (2013.01); *A61D 19/021* (2013.01); *A61L 29/06* (2013.01); *A61M 25/0068* (2013.01); *A61M 2025/0004* (2013.01); *A61M 2210/1433* (2013.01)

(58) Field of Classification Search
CPC .... A61D 19/027; A61D 19/02; A61D 19/021; A61M 2025/0004; A61M 2025/0096; A61M 2210/1433; A61M 2210/1475
See application file for complete search history.

(56) References Cited

U.S. PATENT DOCUMENTS

| | | | |
|---|---|---|---|
| 5,935,098 A | 8/1999 | Blaisdell | |
| 6,695,767 B2 | 2/2004 | Garcia et al. | |
| 7,833,147 B2* | 11/2010 | Graham | G01N 15/1463 600/35 |
| 9,888,990 B2 | 2/2018 | van der Steen | |
| 2007/0055094 A1 | 3/2007 | Chen | |
| 2007/0185558 A1 | 8/2007 | Hartley | |
| 2011/0282135 A1* | 11/2011 | Waybright | A61D 19/027 600/35 |
| 2012/0046260 A1* | 2/2012 | Lee-Sepsick | A61F 6/225 514/249 |
| 2015/0133737 A1 | 5/2015 | Bacich | |

FOREIGN PATENT DOCUMENTS

| | | |
|---|---|---|
| WO | 01/52767 A1 | 7/2001 |
| WO | 2009097872 A1 | 8/2009 |

OTHER PUBLICATIONS

Australian Examination Report dated Mar. 18, 2022 in related AU Appl. No. 2019333169.
Extended European Search Report dated Apr. 20, 2022 in related EP Appl. No. 19856348.8.
Minitube Catalog "Animal Reproduction Technology Porcine." 2019.
International Search Report Opinion dated Nov. 19, 2019 in related WO Appl. No. PCT/US19/48889.

* cited by examiner

*Primary Examiner* — Deanna K Hall
(74) *Attorney, Agent, or Firm* — Ryan Christensen; Hashim Rahman

(57) ABSTRACT

The invention encompasses improved catheters comprised of multiple tubular bodies and methods of using them in artificial insemination.

15 Claims, 4 Drawing Sheets

DEVICES AND METHODS FOR ARTIFICIAL INSEMINATION

REFERENCE TO RELATED APPLICATIONS

This application claims the benefit of United States Provisional Patent Application No. 62/725,829 filed Aug. 31, 2018. The entire disclosures of which are incorporated herein by reference.

BACKGROUND

There is a need in the swine industry to reduce the number of sperm cells used in artificial insemination (i.e., low dose insemination). One such need stems from the desire to use sex-sorted sperm in swine. However, in order to make the use of sex-sorted semen more efficient and commercially viable in swine, the number of sperm cells used in artificial insemination must be reduced dramatically relative to the number of sperm cells typically used with conventional, i.e., unsorted, sperm cells. Another need for low dose insemination stems from the desire to use sperm cells from elite, or high-indexing, boars, whose sperm cells are in limited supply. While laparoscopic insemination techniques allow for the use of small sperm cell doses, such techniques are relatively expensive and generally require the presence of veterinarian. Additionally, such techniques may introduce infection and may stress animals. As such, there is a need to improve the non-invasive devices and methods for low dose insemination in the prior art.

SUMMARY OF THE INVENTION

One embodiment of the invention comprises a catheter comprising a first tubular body, a cervical anchor connected to an outer surface of the first tubular body, and a second tubular body axially and slidably extending within the first tubular body, the second tubular body comprising flexible, polyether block amide and a proximal end and a distal end, the distal end comprising an orifice formed i) in a beveled, radiused or chamfered terminus or ii) in a terminal flange comprising a beveled, radiused or chamfered edge. In a further embodiment, the second tubular body has an outer diameter between 1.5 mm and 5 mm. In a yet further embodiment, the second tubular body has an inner diameter between 0.5 mm and 1.5 mm. In another embodiment, the second tubular body has a hardness between 30 (Shore D) and 70 (Shore D). In an additional embodiment, the second tubular body has a wall thickness between 1.0 mm and 2.0 mm. In a further embodiment, the second tubular body has a hardness between 40 (Shore D) and 60 (Shore D), an outer diameter between 1 mm and 3 mm, and an inner diameter between 0.2 mm and 1.3 mm. In a specific embodiment, the flexible, polyether block amide is comprised of PEBAX®. In a further embodiment, the distal end of the second tubular body comprises a substantially hook-like or u-shaped portion.

Another aspect of the invention encompasses a method of depositing or collecting a fluid, an embryo or gametes, using a catheter, the catheter comprising a first tubular body, a cervical anchor connected to an outer surface of the first tubular body, and a second tubular body axially and slidably extending within the first tubular body, the second tubular body comprising flexible, polyether block amide and a proximal end and a distal end, the distal end comprising an orifice formed i) in a beveled, radiused or chamfered terminus or ii) in a terminal flange comprising a beveled, radiused or chamfered edge, the method comprising inserting the first tubular body into a sow's vagina, advancing the first tubular body into the sow's cervical canal so that the cervical anchor is seated against the cervical canal, advancing the second tubular body axially within the first tubular body, past the cervix, and applying positive or negative pressure within the second tubular body. In a further embodiment, in the step of advancing the second tubular body, the second tubular body is advanced at least 600 mm into a uterine horn. In an even further embodiment, the method comprises a step of depositing $300 \times 10^6$ or less sperm cells into the uterine horn or depositing $150 \times 10^6$ or less sperm cells into the uterine horn. In a particular embodiment, the deposited sperm is sex-sorted sperm. In another embodiment of this method, the flexible, polyether block amide is comprised of PEBAX®. In a yet further embodiment, the deposited sperm cells are from a high indexing boar. In another embodiment, the method also comprises the step of freezing and thawing the sperm cells prior to the step of depositing the sperm cells.

A further embodiment of the invention comprises a catheter comprising a first tubular body, a second tubular body and a third tubular body, the third tubular body axially and slidably extending within the first tubular body, and the second tubular body axially and slidably extending within the third tubular body, the third tubular body comprising a proximal end, a distal end and a deflecting element at the distal end. In a further embodiment, the catheter also comprises a cervical anchor connected to an outer surface of the first tubular body. In an even further embodiment, the second tubular body is comprised of a polyether block amide. In a specific embodiment, the second tubular body has a hardness between 30 (Shore D) and 60 (Shore D), an outer diameter between 1 mm and 3 mm, and an inner diameter between 0.2 mm and 1.5 mm. In a particular embodiment, the polyether block amide is comprised of PEBAX®. In a further embodiment, the distal end of the second tubular body comprises a substantially hook-like or u-shaped portion Another embodiment of the invention comprises a catheter comprising a first tubular body, a second tubular body, a third tubular body and a fourth tubular body, the third tubular body axially and slidably extending within the fourth tubular body, the fourth tubular body axially and slidably extending within the first tubular body and the second tubular body axially and slidably extending within the third tubular body, the third tubular body comprising a proximal end, a distal end and a deflecting element at the distal end. In a further embodiment, the first tubular body comprises a cervical anchor connected to an outer surface of the first tubular body. In a yet further embodiment, the second tubular body is comprised of a polyether block amide. In a specific embodiment, the second tubular body has a hardness between 30 (Shore D) and 60 (Shore D), an outer diameter between 1 mm and 3 mm, and an inner diameter between 0.2 mm and 1.5 mm. In an even more specific embodiment, the polyether block amide is comprised of PEBAX®. In a further embodiment, the distal end of the second tubular body comprises a substantially hook-like or u-shaped portion.

Any of the various embodiments of the invention described above and hereinafter may be applied to, or comprise, individuals or species of non-human mammals, and the invention should be understood not to be limited to the species of non-human mammals described by the specific examples within this application. Rather the specific examples within this application are intended to be illustrative of the varied and numerous species of non-human mammals to which the devices and methods of the invention may be applied. Embodiments of the invention, for example, encompass and may be adapted for use in animals having commercial value for meat or dairy production such as swine, ovine, bovine, equine, deer, elk, buffalo, or the like (naturally the mammals used for meat or dairy production may vary from culture to culture). They also encompass various domesticated non-human mammalian species such as canines and felines, as well as primates, including but not limited to, chimpanzees, and gorillas, as well as whales, dolphins and other marine mammals. In particular embodiments of any of the above disclosed embodiments, the non-human mammalian species comprises swine.

DETAILED DESCRIPTION OF THE INVENTION

The invention encompasses a catheter as well as a method of depositing or collecting a fluid, an embryo or gametes, using a catheter. FIGS. 1 to 5 represent various embodiments of the invention and are described below.

Figure 1:
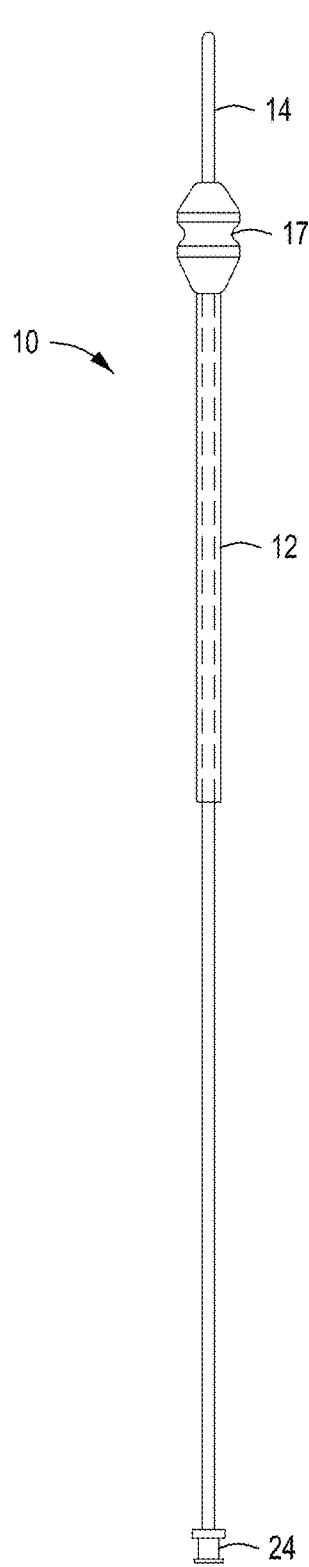
FIG. 1 shows an embodiment of the invention comprising a catheter having two tubular bodies.
Figure 2A:
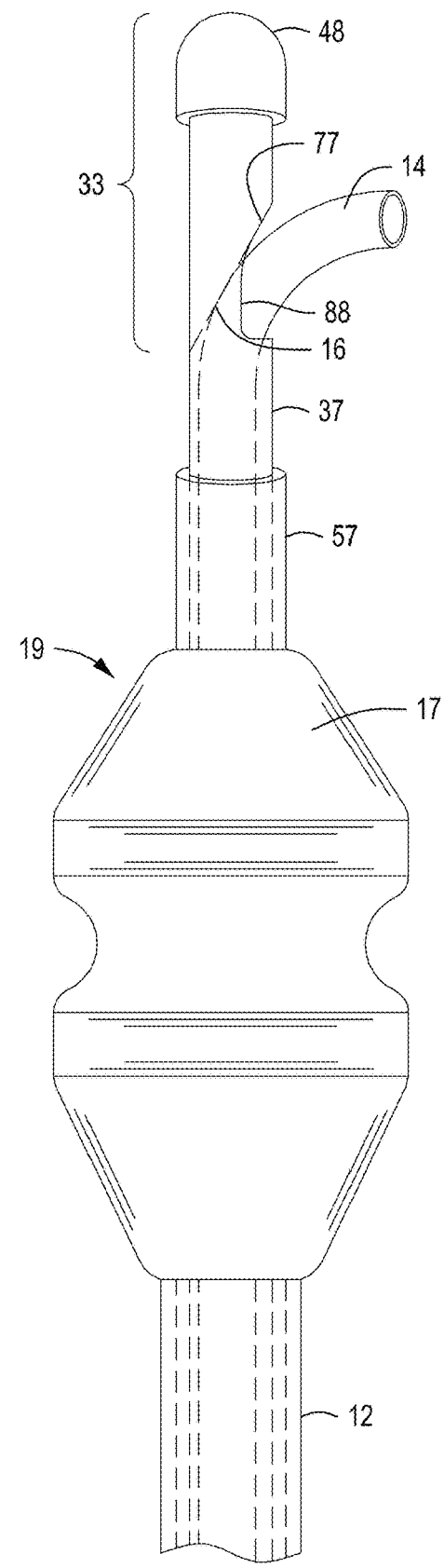
FIG. 2A shows an embodiment of the invention comprising a catheter having four tubular bodies and a deflecting element.
Figure 2B:
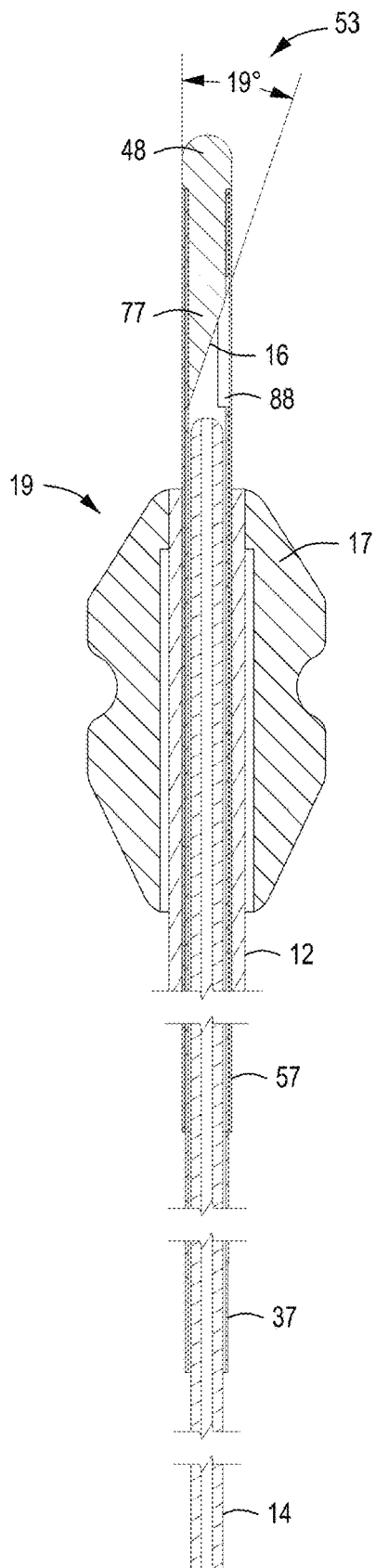
FIG. 2B shows a lateral cross-sectional view of one embodiment of the invention comprised of four tubular bodies and a deflecting element.

In the two embodiments shown in FIGS. 1, 2A, and 2B, respectively, the device is comprised of at least a first tubular body 12 and a second tubular body 14. In FIGS. 2A and 2B, the device is shown to further comprise a third tubular body 37 and a fourth tubular body 57. In each of the embodiments shown in FIGS. 1 and 2A and 2B, the second tubular body 14 serves to transmit fluid, gametes (e.g., sperm cells) or embryos within its lumen, to or from an intrauterine (i.e., post-cervical) location. In contrast, the first tubular body 12, the third tubular body 37 and the fourth tubular body 57, function to guide the second tubular body 14 within a sow's reproductive tract (as used herein, the term "sow" is equivalent to a female swine, including a gilt), including the vagina, cervix and uterine body, and do not directly contact fluid, gametes or embryos transmitted by the second tubular body 14. In each of FIGS. 1 and 2, the second tubular body 14 has an outer diameter that is smaller than the inner diameter of the first tubular body 12 (FIG. 1) and the third tubular body 37 and the fourth tubular body 57 (FIGS. 2A and 2B), so that the second tubular body 14 is able to slide axially within the first tubular body 12 or the third tubular body 37 as the case may be.

In some embodiments of the invention, the second tubular body 14 is comprised of a flexible, polyether block amide, which allows the second tubular body 14 to be advanced deep within a sow's uterine horn without kinking and without risk of damaging the sow's uterus or uterine horns. In a specific embodiment, the polyether block amide is comprised of PEBAX® (Arkema Specialty Polyamides, Colombes, France), including a polyether block amide selected from the PEBAX® 33 Series (hardness between 40 to 70 (Shore D)). In a more specific embodiment, the second tubular body 14 is comprised of PEBAX® 4033 SA 01 material, which has the following characteristics:

TABLE 1

| Property | Typical Value | Unit | Test Method |
| --- | --- | --- | --- |
| Density | 1.00 | g/cm$^3$ | ISO 1183 |
| Water Absorption at Equilibrium | | | |
| At 20° C. and 50% R.H. | 0.5 | % | ISO 62 |
| Water Absorption | | | |
| At 23° C. and 24 h in water | 1.2 | % | |
| Melting Point | 160 | ° C. | ISO 11357 |
| Vicat Point | | | |
| Under 1 daN | 131 | ° C. | ISO 306 |
| Shrinkage (after 24 h, 4 mm, mold at 40° C.) | | | |
| parallel | 0.4 | % | |
| perpendicular | 1.1 | % | |
| Hardness (*) | | | |
| Instantaneous | 90/42 | Shore A/Shore D | ISO 868 |
| After 15 s | 89/35 | Shore A/Shore D | |
| Tensile Test (*) | | | |
| Stress at Break | 40 | MPa | ISO 527 |
| Strain at Break | >450 | % | |
| Flexural Modulus (*) | 77 | MPa | ISO 178 |
| Charpy Impact (*) | | | |
| Unnotched 23° C. | No break | kJ/m$^2$ | ISO 179 |
| Unnotched −30° C. | No break | kJ/m$^2$ | |
| V-notched 23° C. | No break | kJ/m$^2$ | |
| V-notched −30° C. | No break | kJ/m$^2$ | |

PEBAX® 4033 SA 01 MED is processed under the following conditions:

TABLE 2

| Conditions | Typical Values |
| --- | --- |
| Extrusion | |
| Melt Temperature (Min/Recommended/Max) | 210° C./220° C./230° C. |
| Injection | |
| Melt Temperature (Min/Recommended/Max) | 200° C./240° C./270° C. |

TABLE 2-continued

| Conditions | Typical Values |
|---|---|
| Mold | |
| Temperature | 10-30° C. |
| Drying | |
| Time | 4 to 8 hours |
| Temperature | 60 to 70° C. |

Figure 3A:
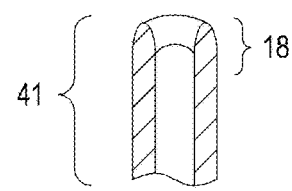
FIG. 3A shows a lateral cross-sectional view of a distal end of a tubular body having a radiused terminus.
Figure 3B:
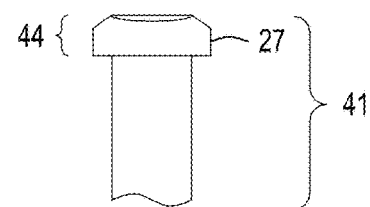
FIG. 3B shows a lateral cross-sectional view of a distal end of a tubular body having a terminal flange with a chamfered edge.

Referring now to FIG. 3A, in this embodiment, the distal end 41 of second tubular body 14 comprises an orifice formed in a radiused terminus 18. In other embodiments, not shown, the second tubular body 14 can comprise an orifice formed in a chamfered terminus or a beveled terminus. In an alternative embodiment shown in FIG. 3B, the second tubular body 14 comprises an orifice formed in a terminal flange 44 comprising a chamfered edge 27. In a further embodiment, not shown, the terminal flange 44 can comprise a beveled edge. In a further embodiment, as depicted in FIG. 5B, the second tubular body 14 can comprise an elliptical orifice 19 formed by a cutting plane that is angled/tilted with respect to the second tubular body's 14 longitudinal axis.

In certain embodiments, the second tubular body 14 has an outer diameter between 1.5 mm and 5 mm. The diameter must be sufficiently small so as to allow the second tubular body 14 to be able to pass through the cervix. Other variables governing dimensions of the second tubular body 14 include the type of material to be transmitted and the target location for the deposition or retrieval of that material. For example, viscous liquids may require that the second tubular body 14 have a relatively larger lumen. For the transmission of fluid, gametes or embryos, in certain embodiments of the invention the second tubular body 14 has an inner diameter between 0.2 mm and 1.5 mm, and in a more specific embodiment, between 0.5 mm and 1.3 mm. The target location for the deposition or retrieval will affect the length, hardness and wall thickness of the second tubular body 14 for a given outer diameter. For example, in order to reach the utero-tubal junction, the second tubular body 14 should be at least 100 cm to 300 cm in length. In some embodiments the second tubular body 14 is at least 110 cm, at least 120 cm, at least 130 cm, at least 140 cm, at least 150 cm, at least 160 cm, at least 170 cm, at least 180 cm, at least 190 cm, at least 200 cm, at least 210 cm, at least 220 cm, at least 230 cm, at least 240 cm or at least 250 cm in length. Additionally, in order to reach the utero-tubal junction or any other distant anatomical target, the second tubular body 14 must be supple enough to traverse the extremely tortuous uterine horn without damaging it and yet resilient enough to resist kinking, which would compromise the second tubular body's 14 ability to transmit the desired material. Accordingly, in certain embodiments of the invention, the second tubular body 14 has a hardness between 30 (Shore D) and 70 (Shore D), and in a more specific embodiment, between 40 (Shore D) and 60 (Shore D), and a wall thickness between 1.0 mm and 2.0 mm. In a very specific embodiment, the second tubular body 14 has a hardness of between 30 to 50 (Shore D), an outer diameter between 2.5 mm and 3.0 mm, and an internal diameter between 1.0 mm and 1.5 mm. As shown in the embodiment in FIG. 1, the second tubular body 14 also comprises a connector 24 at its proximal end for coupling a fluid delivery device, such as a syringe, to the second tubular body 14.

The first tubular body 12, the third tubular body 37, and the fourth tubular body 57 are comprised of any suitable polymer material and in certain embodiments are relatively more rigid than the second tubular body 14. Having sufficient rigidity, the first tubular body 12, third tubular body 37 and fourth tubular body 57 can independently be advanced into, and past, a sow's cervix, which imposes substantial resistance on catheters generally. In some embodiments, the first tubular body 12 is 40 cm to 60 cm in length and between 10 cm to 20 mm in outer diameter. The third tubular body 37 and the fourth tubular body are 60 cm to 75 cm in length in some embodiments of the invention. The third tubular body 37 has an outer diameter of 4 mm and an inner diameter of 3.5 mm in some embodiments. In other embodiments, the third tubular body 37 has an outer diameter of 3 mm to 5 mm and an inner diameter of 2.5 mm to 4.5 mm. The fourth tubular body 57 has an outer diameter of 4.58 mm and an inner diameter of 4.15 mm in some embodiments. In other embodiments, the fourth tubular body 57 has an outer diameter of 3.5 mm to 5.5 mm and an inner diameter of 3.15 mm to 5.15 mm.

In certain embodiments, the first tubular body 12 can also comprise a cervical anchor 17 at its distal end, as shown in FIGS. 1, 2A and 2B. The cervical anchor 17 is of a shape and material (for example, a soft foam polymer) that substantially conforms to the inner walls of the distal portion of the cervical canal so as to stably and reversibly anchor or "lock" the first tubular body 12 in the cervical canal. Use of a cervical anchor 17 also minimizes the risk of backflow of fluids introduced via the second tubular body 14 into the uterus and minimizes the risk of inadvertently entering the urethra as the distal end of the first tubular body 12 is advanced in the reproductive tract. The cervical anchor 17 can be bonded to the outer surface of the first tubular body 12 using adhesive or a suitable bonding method. Alternatively, in some embodiments (not shown), the cervical anchor 17 can be molded as part of the first tubular body 12.

Figure 2C:
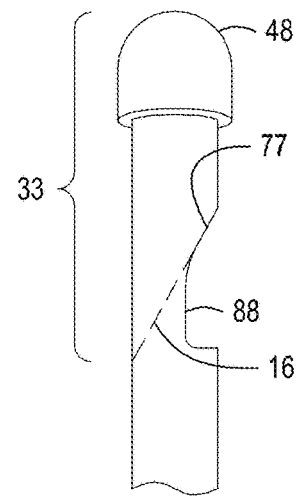
FIG. 2C shows an embodiment of a deflecting element.
Figure 4A:
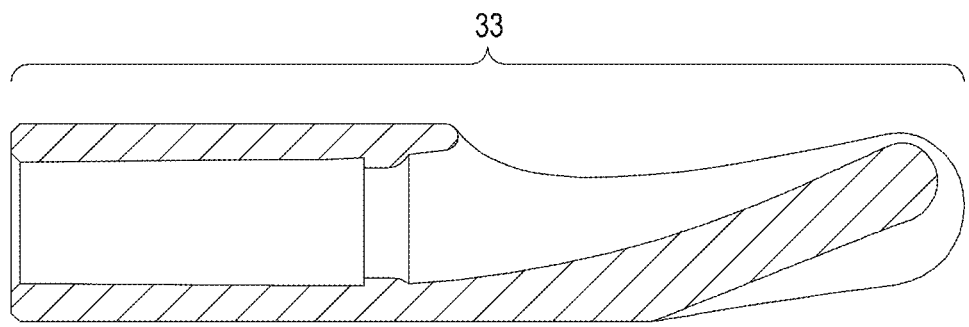
FIG. 4A shows a lateral cross-sectional view of a deflector element having a contoured notch.
Figure 4B:
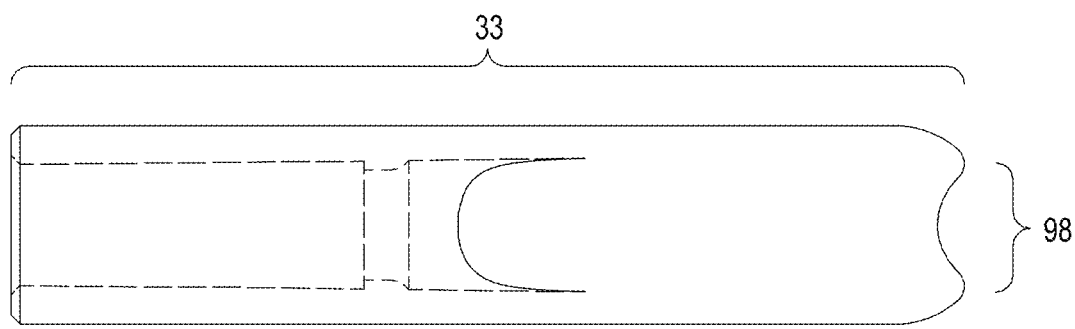
FIG. 4B shows a lateral view of an embodiment of a deflector element having a contoured notch.
Figure 4C:
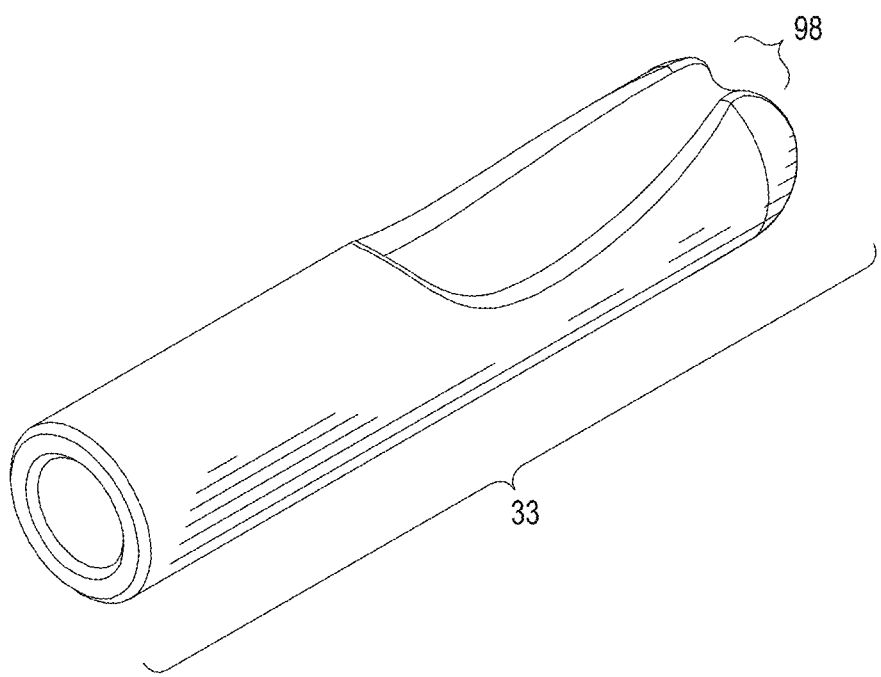
FIG. 4C shows a perspective view of an embodiment of a deflector element having a contoured notch.

As shown in FIGS. 2A and 2B, the third tubular body 37 comprises a deflecting element 33 at its distal end. As used herein, the term "deflecting element" comprises a surface at an angle to the longitudinal axis of the third tubular body 37 of which it is a part. The deflecting element 33 as depicted in FIGS. 2A to 2C comprises a ramp 77. As shown in FIGS. 2A to 2C, the deflecting element 33 further comprises an aperture 88, through which the second tubular body 14 passes as the second tubular body is axially advanced within the third tubular body 37. As shown in FIG. 2B, the surface 16 of ramp 77 forms an angle 53 relative to the longitudinal axis of the third tubular body 37. In the embodiment shown in FIG. 2B, the angle 53 is approximately 19 degrees. In other embodiments (not shown), the angle 53 can be between 10 to 30 degrees, between 15 to 25 degrees, or between 17 to 23 degrees. A further embodiment of the invention is depicted in FIGS. 4A to 4C, in which deflecting element 33 comprises a contoured notch 98.

As shown in FIG. 2A, as the second tubular body 14 is axially advanced within the third tubular body 37, the deflecting element 33 causes the second tubular body 14 to exit the third tubular body 37 at an angle that matches, or that is approximately equivalent to, angle 53. By deflecting the second tubular body 14 relative to the longitudinal axis of the third tubular body 37, the user can direct the second tubular body 14 into either the left or right uterine horn specifically, which has several advantages. Specifically, for low dose artificial insemination applications (such as when using sex-sorted sperm or sperm from high-indexing boars), the user can now reliably perform bilateral insemination (i.e., deposit sperm in both uterine horns). In certain embodiments (not shown), at their proximal ends, the first tubular body 12, the third tubular body 37 or the fourth tubular body 57, has one or more indexing marks that can be used to ascertain the direction of deflection as the third tubular body 37 is rotated around its longitudinal axis by the user.

Figure 5A:
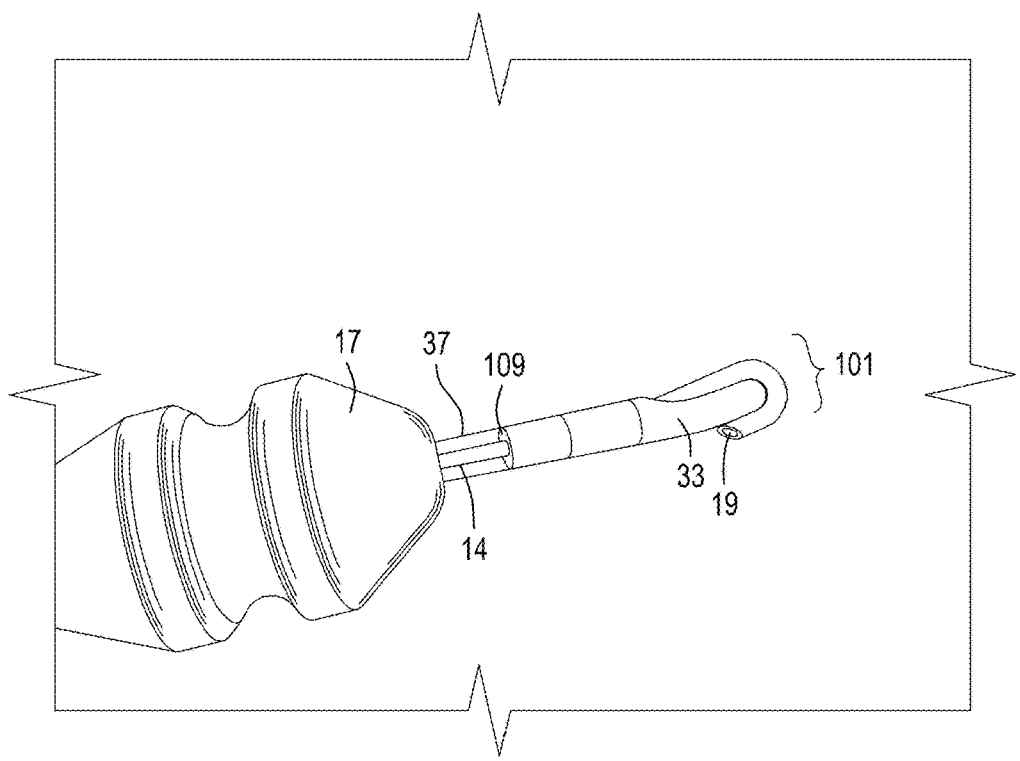
FIG. 5A shows an embodiment of a tubular body having a substantially hook-shaped or u-shaped portion that conforms to the outer contour of a deflecting element.
Figure 5B:
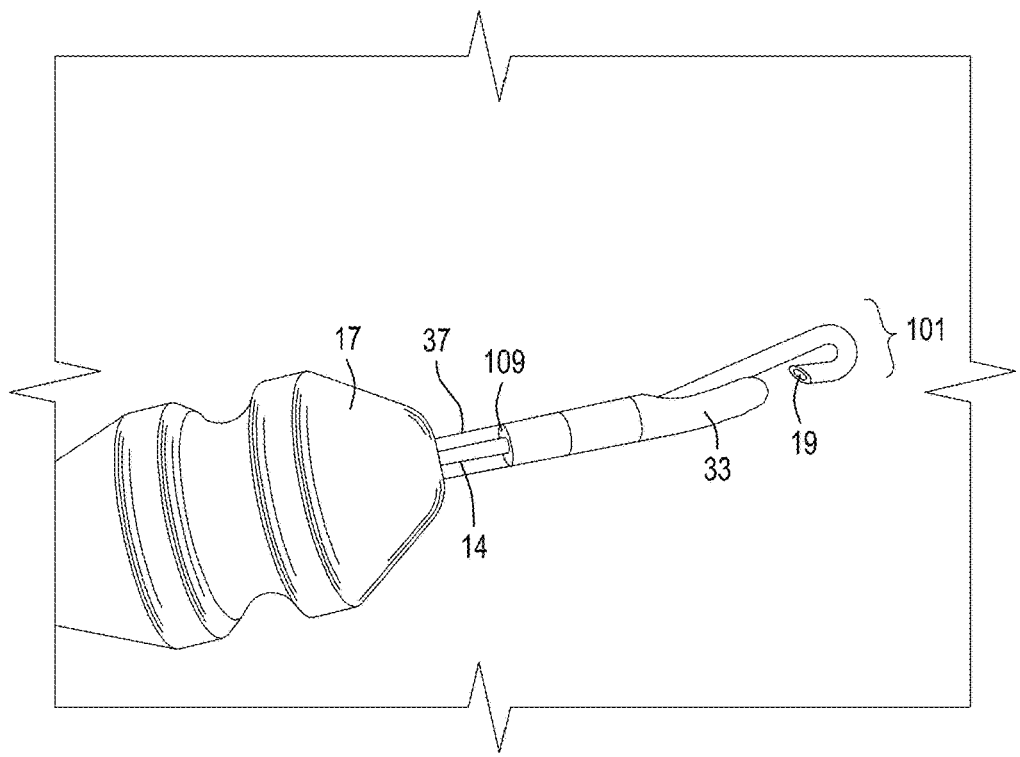
FIG. 5B shows an embodiment of a tubular body having a substantially hook-shaped or u-shaped portion that conforms to the outer contour of a deflecting element and in which the hook-shaped or u-shaped portion has been axially advanced away from the deflector element.

In another embodiment of the invention, depicted in FIGS. 5A and 5B, the distal end of the second tubular body 14 comprises a substantially hook-like or u-shaped portion 101 that serves to bend the distal end of the lumen of the second tubular body 14 back in the direction of the proximal end of the second tubular body 14. As shown in FIG. 5A, in a certain embodiment of the invention, the substantially hook-like or u-shaped portion 101 substantially conforms to the distal end of deflecting element 33 (which may optionally further comprise contoured notch 98 within which the curved portion of the substantially hook-like or u-shaped portion 101 of the second tubular body 14 may rest). In certain embodiments, the overall width of the substantially hook-like or u-shaped portion 101 at its widest dimension is between, 2 mm to 10 mm, 2 mm to 8 mm, 2 mm to 7 mm, 2 mm to 5 mm, 3 mm to 10 mm, 3 mm to 8 mm, 3 mm to 7 mm, or 3 mm to 5 mm. In an alternative embodiment of the invention, not shown, the distal end of the second tubular body 14 comprises an inflatable balloon instead of the hook-like or u-shaped portion 101, which can be inflated by the user once the second tubular body 14 has passed into the uterine body, past the cervix.

In certain embodiments, the deflecting element 33 can be bonded to the third tubular body 37 or attached to the third tubular body 37 using a coupling member 109 that fits within the lumen of the third tubular body 37 and the lumen of the deflecting element 33 (as shown in FIGS. 5A and 5B)—the coupling member 109 itself comprising a lumen through which the second tubular body 14 can pass, or alternatively, the deflecting element 33 can be molded as part the third tubular body 37. Additionally, in certain embodiments the deflecting element 33, as shown in FIGS. 2A to 2C may comprise a distal end structure 48 that is radiused in order to prevent injury to the cervix or uterus. The deflecting element 33 can be formed from a polymer material. The surface 16 of the ramp 77 of the deflecting element 33 is at an angle relative to the longitudinal axis of the third tubular body 37, and in various embodiments, can be flat (as shown in FIGS. 2A to 2C), convex or concave (not shown) along the longitudinal axis of deflecting element 33 when viewed in longitudinal cross-section (e.g., FIG. 2B). In some embodiments, the surface 16 is scalloped so as to form a rounded trough so that the terminus 18 of the second tubular body 14 can be advanced smoothly as it transitions across deflecting element 33 and so that the deflecting element 33 can impart greater directional precision to the second tubular body 14 as it is axially advanced within the third tubular body 37.

Referring to FIG. 1, one embodiment of the invention encompasses a catheter 10 comprising a first tubular body 12 and a second tubular body 14. The second tubular body 14 can also comprise a connector 24 as shown in this particular embodiment.

A further aspect of the invention encompasses a method of depositing or collecting a fluid, an embryo, or gametes using the catheter 10 shown in FIG. 1. The method comprises inserting the first tubular body 12 into a sow's vagina; advancing the first tubular body 12 into the sow's cervical canal so that the cervical anchor 17 is seated against the cervical canal; advancing the second tubular body 14 axially within the first tubular body 12, past the cervix; and applying positive or negative pressure (as via a syringe or other suction device) within the second tubular body 14 to either deposit, or collect, fluid, embryos, or gametes as the case may be. In certain embodiments, the second tubular body 14 is advanced at least 600 mm into a uterine horn. In a certain embodiment, it is contemplated that $300 \times 10^6$ or less sperm cells are deposited into a uterine horn, and in a more specific embodiment, it is contemplated that $150 \times 10^6$ or less sperm cells into the uterine horn.

Referring to FIGS. 2A and 2B, one embodiment of the invention encompasses a catheter 19 comprising a first tubular body 12, a second tubular body 14, a third tubular body 37 and a fourth tubular body 57. FIG. 2B is a cross-sectional view of the catheter 19 shown in FIG. 2A. In this embodiment, the third tubular body 37 comprises a deflecting element 33. The second tubular body 14 fits within the lumen of the third tubular body 37; the third tubular body 37 in turn fits within the lumen of the fourth tubular body 57; and the fourth tubular body 57 in turn fits within the first tubular body 12. Accordingly, the second tubular body 14, the third tubular body 37 and the fourth tubular body 57 are each able to be axially advanced within the tubular body within which it immediately sits.

One aspect of the invention is a method of depositing or collecting a fluid, an embryo or gametes using the catheter 19 shown in FIGS. 2A and 2B. The method comprises inserting the first tubular body 12 into a sow's vagina; advancing the first tubular body 12 into the sow's cervical canal so that the cervical anchor 17 is seated against the cervical canal; advancing the fourth tubular body 57 axially within the first tubular body 12, past the cervix; advancing the third tubular body 37 axially within the fourth tubular body 57 sufficiently to expose the aperture 88 of the third tubular body 37 to the interior of the uterine body; advancing the second tubular body 14 axially within the third tubular body 37, out of the aperture 88 and into a uterine horn; and applying positive or negative pressure within the second tubular body 14. A further embodiment of the method comprises the additional step of withdrawing the second tubular body 14 from the uterine horn, rotating the third tubular body 37 around its longitudinal axis and then advancing the second tubular body 14 into the contralateral uterine horn in order to deposit or collect a fluid, an embryo or gametes in the contralateral uterine horn. In a particular embodiment, the second tubular body 14 is advanced at least 600 mm into a uterine horn. A further embodiment encompasses depositing $300 \times 10^6$ or less sperm cells into each uterine horn or depositing $150 \times 10^6$ or less sperm cells into each uterine horn.

Another aspect of the invention encompasses a further embodiment of the above-described methods in which the second tubular body 14 comprises a distal end having a substantially hook-like or u-shaped portion 101. In this particular embodiment, the substantially hook-like or u-shaped portion 101 of the second tubular body 14 rests over the deflector tip 33 of the third tubular body 37 as the third tubular body 37 is advanced into the cervix.

Example 1

The purpose of this example was to 1) test the effect of semen deposition site (uterine body vs horns); 2) test the effect of stepwise reduction of sperm dose quantity; and 3) test the effect of insemination-to-ovulation interval (synchronize ovulation for 1 fixed-time artificial insemination ("AI") using transrectal ultrasound to monitor follicle disappearance and PHENICOL® 6000 (pregnant mare serum gonadotrophin/equine chorionic gonadotrophin ("PMSG/eCG")) and OVUGEL® (GnRH agonist).

Semen was collected from three boars and pooled. 635 sows were split between 8 treatment groups based on location of deposition of the AI sperm dose (i.e., the body of the uterus vs. the uterine horn) and number of sperm cells in the AI dose (ranging 1.2 billion to 75 million sperm cells per dose).

Sows received a 2 mL IM injection (18 gauge, 1.5" needle) approximately 0.5" lateral to the vulva of either 600 IU of eCG (PREGNECOL® 6000, Vetoquinol-Calier, Lavaltrie, Quebec) or a sterile saline vehicle alone. At 3:00 to 5:00 PM on day 3 post-weaning (Thursday and Sunday), sows' ovaries were scanned by transrectal ultrasound (Aloka 500+UST-5561 7.5 MHz transducer fixed on a custom PVC handle) to estimate average follicular diameter. Detection of estrus by the back-pressure test (BPT) during boar exposure controlled by a boar cart were also performed at that time. At 5:00 PM (80 h post-weaning), all sows received an intravaginal infusion of 2 mL of OVUGEL® (200 mcg triptorelin acetate). At 3:00 to 5:00 PM on day 4 post-weaning (Friday and Monday), one more BPT was performed and sows were scanned at that time and for every 8 hours (12:00 midnight; 8:00 AM; 4:00 PM) to document time of ovulation. Regardless of estrus, all sows received one insemination, around 4:00 to 6:00 pm (24 to 26 h post-OVUGEL®), in accordance with one of the 8 treatment groups.

Insemination in the uterine body was accomplished using a conventional post-cervical AI catheter. Conversely, insemination in the uterine horns was accomplished using a catheter of the invention (comprising two tubular bodies, with the first tubular body with a cervical anchor, and the second tubular body comprising PEBAX® 4033 SA 01 MED (hardness of 40 (Shore D)) and having a length of 254 cm, an inner diameter of 1.27 mm and an outer diameter of 2.794 mm. Insemination in a uterine horn was accomplished by advancing the first tubular body into the cervix and once properly seated, advancing the second tubular body until it could not be advanced any further into the reproductive tract. Table 3, below, shows the results for each treatment group in terms of pregnancy rate and the average number of viable and non-viable embryos for each sow.

TABLE 3

| AI Trt | Spz, Bill | Site Depo | Dose + Flush, mL | Sows, n = | Pregnant, % | Viable Embryos | Non-Viable Embryos | Preg × Viable | Embryo Mort, % |
|---|---|---|---|---|---|---|---|---|---|
| 1 | 1.2 | Body | 40 | 67 | 81.4 ± 5.1 | 14.7 ± 0.6$^a$ | 1.6 ± 0.2$^a$ | 12.0 | 31.2 ± 2.8$^a$ |
| 2 | 0.6 | Body | 20 + 20 | 70 | 84.1 ± 4.6 | 13.6 ± 0.6$^{ab}$ | 1.9 ± 0.2$^a$ | 11.4 | 37.0 ± 2.7$^{ab}$ |
| 3 | 0.6 | Horn | 20 | 66 | 78.7 ± 5.2 | 13.1 ± 0.6$^{abc}$ | 1.8 ± 0.2$^a$ | 10.3 | 39.5 ± 2.9$^{bc}$ |
| 4 | 0.3 | Body | 10 + 30 | 62 | 78.0 ± 5.4 | 11.6 ± 0.6$^{cd}$ | 1.5 ± 0.2$^a$ | 9.0 | 45.6 ± 2.9$^{cde}$ |
| 5 | 0.3 | Horn | 10 + 10 | 71 | 83.3 ± 4.6 | 12.1 ± 0.6$^{bcd}$ | 1.5 ± 0.2$^a$ | 10.1 | 43.4 ± 2.7$^{bcd}$ |
| 6 | 0.15 | Body | 5 + 35 | 68 | 76.7 ± 5.4 | 10.8 ± 0.6$^d$ | 1.5 ± 0.2$^a$ | 8.3 | 49.7 ± 2.9$^{de}$ |
| 7 | 0.15 | Horn | 5 + 15 | 65 | 87.7 ± 4.3 | 11.3 ± 0.6$^d$ | 1.6 ± 0.2$^a$ | 9.9 | 47.5 ± 2.8$^{de}$ |
| 8 | 0.075 | Horn | 2.5 + 17.5 | 64 | 75.0 ± 5.8 | 10.4 ± 0.6$^d$ | 1.2 ± 0.2$^b$ | 7.8 | 51.6 ± 3.0$^e$ |

Within a column, means that have no superscript in common are significantly different from each other P < .05

Table 4, below, shows the pregnancy rates achieved for each ovulation group (ovulation 18.5 to 34.5 hours after OVUGEL® treatment; 38.5 to 42.5 hours after OVUGEL® treatment; 46.5 to 54.0 hours after OVUGEL® treatment; or 55 or more hours after OVUGEL® treatment) as a function of sperm dose.

TABLE 4

| AI Trt | Spz, Bill | Sows, n = | 18.5 to 34.5 (6 h) | 38.5 to 42.5 (17 h) | 46.5 to 54.0 (24 h) | ≥55.0 (?? h) |
|---|---|---|---|---|---|---|
| 1 | 1.2 | 67 | 83.5 ± 10.9 | 86.3 ± 5.8 | 84.8 ± 10.1 | 55.2 ± 17.8 |
| 2&3 | 0.6 | 136 | 61.9 ± 12.3$^a$ | 92.4 ± 3.0$^b$ | 87.0 ± 7.2$^b$ | 27.7 ± 10.9$^c$ |
| 4&5 | 0.3 | 133 | 80.7 ± 8.9$^{ab}$ | 90.0 ± 3.6$^a$ | 74.9 ± 9.1$^{bc}$ | 51.0 ± 13.0$^c$ |
| 6&7 | 0.15 | 133 | 77.2 ± 9.3$^a$ | 82.7 ± 4.5$^a$ | 89.9 ± 5.6$^a$ | 39.5 ± 15.3$^b$ |
| 8 | 0.075 | 64 | 83.1 ± 15.5 | 80.5 ± 6.4 | 81.4 ± 12.2 | |
| All | | 33 | 76.0 ± 5.2$^a$ | 86.9 ± 2.1$^b$ | 83.7 ± 3.9$^{ab}$ | 36.5 ± 6.4$^c$ |

Within a row, means with no superscript in common are significantly different from each other P < .05

Effect of AI Trt, = .42; Ovclass, <.0001; Lact, <.05

Effect of AI Trt × Ovclass, <.0001; Lact, <.03

Table 5, below, shows the average number of embryos obtained from sows within each ovulation group as a function of sperm dose.

TABLE 5

| AI Trt | Spz, Bill | Sows, n = | 18.5 to 34.5 (6 h) | 38.5 to 42.5 (17 h) | 46.5 to 54.0 (24 h) | ≥55.0 (?? h) |
|---|---|---|---|---|---|---|
| 1 | 1.2 | 67 | 17.9 ± 1.6 | 16.1 ± 0.9 | 17.5 ± 1.6 | 13.4 ± 2.7 |
| 2&3 | 0.6 | 136 | 16.8 ± 1.5 | 15.4 ± 0.6 | 15.2 ± 1.1 | 13.4 ± 2.1 |
| 4&5 | 0.3 | 133 | 13.3 ± 1.1 | 13.5 ± 0.6 | 14.3 ± 1.2 | 12.3 ± 1.6 |
| 6&7 | 0.15 | 133 | 12.7 ± 1.2$^{ab}$ | 13.5 ± 0.6$^a$ | 10.6 ± 1.0$^b$ | 13.8 ± 2.3$^{ab}$ |
| 8 | 0.075 | 64 | 12.2 ± 2.1 | 11.2 ± 0.9 | 13.3 ± 1.7 | |
| All | | 533 | 14.4 ± 0.6 | 14.0 ± 0.3 | 13.8 ± 0.6 | 12.7 ± 1.1 |

Within a row, means with no superscript in common are significantly different from each other P < .05
Effect of AI Trt, <.0001; Ovclass, = .56; BA, = .0003; ORclass, <.0001
Effect of AI Trt × Ovclass, = .54

Example 2

The purpose of this example was to determine the distance that a catheter of the invention could be advanced in a sow's reproductive tract compared with a catheter comprised of metal and polymer (DeepBlue porcine AI catheter, Ref. 17113/0100, Minitüb GmbH, Tiefenbach, Germany ("Catheter A")). The catheter of the invention was comprised of two tubular bodies, with the first tubular body with a cervical anchor, and the second tubular body comprising PEBAX® 4033 SA 01 MED (hardness of 40 (Shore D)) and having a length of 254 cm, an inner diameter of 1.27 mm and an outer diameter of 2.794 mm. Catheter A had a length of 182.88 cm.

Seven sows in heat were utilized in this example. "Catheter 1" was advanced in the sow's reproductive tract until significant resistance was encountered, and then withdrawn. 40 minutes later, "Catheter 2" was advanced in the same sow's reproductive tract until significant resistance was encountered. A summary of the order in which each sow received Catheter A and the catheter of the invention is provided in Table 6, below.

TABLE 6

| Sow | Catheter 1 | Catheter 2 |
|---|---|---|
| 1 | Cath. A | Invention |
| 2 | Invention | Cath. A |
| 3 | Cath. A | Invention |
| 4 | Invention | Cath. A |
| 5 | Cath. A | Invention |
| 6 | Invention | Cath. A |
| 7 | Cath. A | Invention |

The results of are provided in Table 7, below. In Table 7, the improvement in distance achieved by the catheter of the invention in each sow was standardized to 182.88 cm, the length of Catheter A, so that a more accurate comparison could be made. Additionally, Table 7 provides "% Corrected Improvement," in which the percentage of improvement was corrected by eliminating the results achieved for sows 4 and 7, since for each of those sows, the entire length of Catheter A was able to be advanced into the sow's reproductive tract.

TABLE 7

| Sow | Catheter A Distance Advanced (cm) | Invention Distance Advanced (cm) | Improvement vs Catheter A, standardized to 182.88 (cm) | % Improvement | % Corrected Improvement |
|---|---|---|---|---|---|
| 1 | 160.02 | 254 | 71.12 | 38.89 | 38.89 |
| 2 | 171.45 | 254 | 71.12 | 38.89 | 38.89 |
| 3 | 127 | 231.14 | 48.26 | 26.39 | 26.39 |
| 4 | 182.88 | 213.36 | 30.48 | 16.67 | |
| 5 | 147.32 | 254 | 71.12 | 38.89 | 38.89 |
| 6 | 165.1 | 254 | 71.12 | 38.89 | 38.89 |
| 7 | 182.88 | 200.66 | 17.78 | 9.72 | |
| | | | AVG | 29.76 | 36.39 |
| | | | STDev | 12.37 | 5.59 |

Although the foregoing invention has been described in some detail, one of ordinary skill in the art will understand that certain changes and modifications may be practiced within the scope of the claims.

What we claim is:
1. A catheter comprising:
   a first tubular body;
   a cervical anchor connected to an outer surface of the first tubular body; and
   a second tubular body axially and slidably extending within the first tubular body, the second tubular body comprising
      a lumen;
      a polyether block amide and
      a proximal end and a distal end, the distal end comprising a u-shaped portion, wherein the u-shaped portion serves to bend the distal end of the lumen of the second tubular body back in the direction of the proximal end of the second tubular body, and an orifice formed i) in a beveled, radiused or chamfered terminus or ii) in a terminal flange comprising a beveled, radiused or chamfered edge.
2. The catheter of claim 1, wherein the second tubular body has an outer diameter between 1.5 mm and 5 mm.
3. The catheter of claim 1, wherein the second tubular body has an inner diameter between 0.5 mm and 1.5 mm.
4. The catheter of claim 1, wherein the second tubular body has a hardness between 30 (Shore D) and 70 (Shore D).
5. The catheter of claim 1, wherein the second tubular body has a wall thickness between 1.0 mm and 2.0 mm.
6. The catheter of claim 1, wherein the second tubular body has a hardness between 40 (Shore D) and 60 (Shore D), an outer diameter between 1 mm and 3 mm, and an inner diameter between 0.2 mm and 1.3 mm.

7. The catheter of claim 1, wherein the polyether block amide is comprised of PEBAX®.

8. A method of depositing or collecting a fluid, an embryo or gametes using a catheter, the catheter comprising a first tubular body, a cervical anchor connected to an outer surface of the first tubular body, and a second tubular body axially and slidably extending within the first tubular body, the second tubular body comprising a lumen, a polyether block amide and a proximal end and a distal end, the distal end comprising a u-shaped portion, wherein the u-shaped portion serves to bend the distal end of the lumen of the second tubular body back in the direction of the proximal end of the second tubular body, and an orifice formed i) in a beveled, radiused or chamfered terminus or ii) in a terminal flange comprising a beveled, radiused or chamfered edge, the method comprising:

inserting the first tubular body into a sow's vagina;

advancing the first tubular body into the sow's cervical canal so that the cervical anchor is seated against the cervical canal;

advancing the second tubular body axially within the first tubular body, past the sow's cervix; and applying positive or negative pressure within the second tubular body.

9. The method of claim 8, wherein in the step of advancing the second tubular body, the second tubular body is advanced at least 600 mm into a uterine horn.

10. The method of claim 9, further comprising the step of depositing $300 \times 10^6$ or less sperm cells into the uterine horn.

11. The method of claim 9, comprising depositing $150 \times 10^6$ or less sperm cells into the uterine horn.

12. The method of claim of claim 10, wherein the sperm is sex-sorted sperm.

13. The method of claim 8, wherein the polyether block amide is comprised of PEBAX®.

14. The method of claim 10, wherein the sperm cells are from a high indexing boar.

15. The method of claim 10, further comprising the step of freezing and thawing the sperm cells prior to the step of depositing.

* * * * *